United States Patent [19]
Kulkarni

[11] Patent Number: 5,387,589
[45] Date of Patent: Feb. 7, 1995

US005387589A

[54] METHOD OF TREATING OCULAR INFLAMMATION

[75] Inventor: Prasad S. Kulkarni, Anchorage, Ky.

[73] Assignee: University of Louisville Research Foundation, Inc., Louisville, Ky.

[21] Appl. No.: 978,188

[22] Filed: Nov. 17, 1992

Related U.S. Application Data

[63] Continuation of Ser. No. 735,604, Jul. 25, 1991, abandoned.

[51] Int. Cl.$^6$ ............................................. A61K 31/44
[52] U.S. Cl. ..................................................... 514/291
[58] Field of Search ......................................... 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,650,803 | 3/1987 | Stella et al. | 514/291 |
| 4,885,171 | 12/1989 | Surendra et al. | 424/122 |
| 5,066,493 | 11/1991 | Sehgal et al. | 424/122 |

FOREIGN PATENT DOCUMENTS 406791  1/1991  European Pat. Off. .

OTHER PUBLICATIONS

Morris et al., Med. Sci. Res. 17:877–878 (1989).
Martel et al., Inhibition of Immune Response by Rapamycin, Can. J. Physiol. Pharmacol. 55: 48–51, 1977.
Morris et al., Identification of New Pharmacologic Action for an Old Compound, Med. Sci. Res. 17: 877–888, 1989.
Sehgal, S. N. and Chang, J. Y. Rapamycin: A New Immunosuppressive Macrolide. Transplantation and Immunology Letter (1990), VII: 12–14.
Calne, R. Y. et al., Rapamycin for Immunosuppression in Organ Allografting. The Lancet (Jul. 22, 1989), p. 227.
Carpenter, Immunosuppression in Organ Transplantation, New England J. of Med. 322: 1224–1226, 1990.
Vezina, C., Kudeiski, A. and Sehgal, S. N., Rapamycin (AY-22, 989). A New Anti-Fungal Antibiotic: I. Taxonomy of the Producing Streptomycete and Isolation of the Active Principle, J. Antibiotics (1975), 28:721–726.
Sehgal, S. N., Baker, H. and Vezina, C., Rapamycin (AY-22, 989). A New Antifungal Antibiotic: II. Fermation, Isolation and Characterization, J. Antibiotics (1975), 28:727–732.
Staruch et al., FK 506 and Rapamycin Inhibit Murine T-cell Activation Through Different Mechanisms, FASEB Journal, vol. 3, Abstract No. 3411, 1989.
Dumont et al., Rapamycin Blocks the Immunosuppressive Effect of FK506 But Not That of Cyclosporin A, FASEB Journal, vol. 3, Abstract No. 5256, 1989.
Kulkarni, P. S., Bhattacherjee, P., Eakins, K. E. and Srinivasan, B. D., Anti-Inflammatory Effects of Betamethasone Phosphate Dexamethasone Phosphate and Indomethacin on Rabbit Ocular Inflammation Induced by Bovine Serum Albumin, Current Eye Res. (1981), 1(1) :43–47.
Kulkarni, et al., Comparative In Vivo Inhibitory Effects of Non-Steroidal In A Non-Steroidal Anti-Inflammatory Agent on Prostaglandin Synthesis in Ocular Tissues, Prostaglandin Synthesis 103: 103–106, 1985.
De Vries et al., Cyclosporin and the Treatment of Severe Chronic Idiopathic Uveitis, Brit. J. Ophthal. 74: 344–349, 1990.
Sears, M. L., Aphakic Cystoid Macular Edema. The Pharmacology of Ocular Trauma. Surv. Ophthalmology (1984), 28: 525–534.
Nussenblatt, R. B., Palestine, A. G., and Chan, C–C. Cyclosporin A Therapy in the Treatment of Intraocular Inflammatory Disease Resistant to Systemic Systemic Corticosteroids and Cytotoxin Agents. Am. J. Ophthal. (1983), 96(3): 275–282.

(List continued on next page.)

*Primary Examiner*—Jerome D. Goldberg
*Attorney, Agent, or Firm*—Darby & Darby

[57] ABSTRACT

Disclosed is a method of treating ocular inflammation in a mammal in need of such treatment, including administering to the mammal an anti-inflammatory amount of rapamycin.

7 Claims, 7 Drawing Sheets

OTHER PUBLICATIONS

Nussenblatt, R. B., Palestine, A. G., Rook, A. H., Scher, I., Wacker, W. B. and Gery, I. Treatment of Intraocular Inflammatory Disease with Cyclosporin A, The Lancet (1983), 2:235–238.

Bhattacherjee, P., William, R. E. and Eakins, K. E. An Evaluation of Ocular Inflammation Following the Injection of Bacterial Endotoxin into the Rat Foot Pad. Invest. Ophthalmol. and Vis. Sci. (1983), 24: 196–202.

Kulkarni, P. and Srinivasan, B. D. Ocular Inflammation: A Pharmacological Model, Trends in Pharmacological Sciences, (1987), 8(10) : 375–377.

Chan, C-C, Caspi, R., Mochizuki, M. et al. Cyclosporine and Dexamethasone Inhibit MHC Class I Antigens and IL-2 Receptor Expression in Experimental Autoimmune Uveitis, Immunological Invest. (1987), 16(4):319–331.

Kulkarni, P. S. and Srinivasan, B. D. Non-Steroidal Anti-Inflammatory Drugs in Ocular Inflammatory Conditions. Lewis, A. and Furst, D. E., eds., New York and Basel, Marcel Dekker, Inc., (1986), pp. 107–155.

Issekutz, T. B. Effects of Anti-Inflammatory Agents on Lymphocyte Migration Stimulated by the Interferons, Tumor Necrosis Factor and Cutaneous Inflammation, Int. J. Immunopharmacol. (1989), 11(7):725–732.

Masferrer, J. L., Zweifel, B. S., Seibert, K. and Needlemen, P. Selective Regulation of Cellular Cyclooxygenase by Dexamethasone and Endotoxin in Mice, J. Clin. Invest. (1990), 86: 1375–1379.

Flower, R. J. and Blackwell, G. J. Anti-Inflammatory Steroids Induce Biosynthesis of a Phospholipase $A_2$ Inhibitor Which Prevents Prostaglandin Generation. Nature (1979), 278: 456–459.

Borel, J. F. Comparative Study In Vitro and In Vivo Drug Effects On Cell Mediated Cytotoxicity. Immunology (1976), 31:631–641.

Guo, A. Ohia, E., Xu, J., Bhattacherjee, P. and Kulkarni, P. S. Effects on Anti-Inflammatory and Immunosuppressive Drugs on the Heterolamellar Corneal Transplantation in Rabbits, Current Eye Res. (1990), 9(8): 749–757.

White, D. J. G. Cyclosporin A. Clinical Pharmacology and Therapeutic Potential, Drugs (1982), 24: 322–334.

Bradford, M. M. A Rapid and Sensitive Method for the Quantitation of Microgram Quantities of Protein . . . Anal. Biochem. (1976), 72:248–254.

Sedmak, J. J. and Grossberg, S. E. A Rapid and Versatile Assay for Protein Using Coomassie Brilliant Blue, Anal. Biochem. (1977), 79–544–552.

Bradley, et al. Measurement of Cutaneous Inflammation: Estimation of Neutrophil Content With an Enzyme Marker. J. Invest. Dermatology (1982), 78:206–209.

EP Search Report for EP 92 11 2716 Collier et al., Current Opinion in Immunol. 2(6):854–858 (1990).

Smith Lang et al., FASEB 6(4):A1048 (1992) Thomson et al., Autoimmunity 12(4):303–313 (1992).

METHOD OF TREATING OCULAR INFLAMMATION

This is a continuation of application Ser. No. 735,604, filed Jul. 25, 1991, abandoned.

FIELD OF THE INVENTION

The present invention relates to the treatment of ocular inflammation. More particularly, the present invention relates to the treatment of ocular inflammation by administration of rapamycin.

BACKGROUND OF THE INVENTION

Ocular inflammation may take the form of numerous eye disorders of varying severity depending on the location of the inflammation. Disorders attributed to ocular inflammation include uveitis, conjunctivitis, episcleritis, scleritis, optic neuritis, retrobulbar neuritis, keratitis, blepharitis, and the like. Many of these conditions occur secondary to bacterial or viral infection.

In ocular bacterial infection, endotoxin (the lipopolysaccharide component of gram negative bacteria) produces ocular inflammation as indicated by conjunctival and iridial hyperemia, breakdown of blood aqueous barrier and polymorphonuclear neutrophil infiltration into the aqueous humor and iris ciliary body. In this type of inflammation, some of the arachidonic acid metabolites of the prostaglandins and leukotrienes have been implicated as inflammatory mediators. Other studies have also demonstrated that additional inflammation may be caused by the secondary induction of the expression of major histocompatibility complex Class II (Ia) antigens in the iris ciliary body.

Ocular inflammation can also result following ophthalmologic surgical procedures or ocular trauma resulting from physical injury of the eye.

Uveitis is typical of these ocular disorders, and is characterized by inflammation of the uveal tract, which encompasses the iris, ciliary body, and choroid. Retinal inflammation is also classified as a type of uveitis. Uveitis may be anatomically classified as anterior (iritis and iridocyclitis), intermediate (cyclitis and peripheral uveitis), posterior (choroiditis and retinitis) and diffuse (iritis plus intermediate uveitis plus chorioretinitis). Merck Manual, 15th ed., 2227 (1987).

Repeated episodes of anterior uveitis, for example, can cause permanent and severe damage to the internal structures of the eye with grave consequences. For example, recurrent anterior uveitis may lead to the formation of considerable peripheral anterior synechia and secondary glaucoma. Chronic anterior uveitis can also cause corneal endothelial dysfunction and even cataract formation. Posterior inflammation can lead to persistent pathological vitreous alteration and retinal dysfunction, either of which may result in intractable visual loss.

It is well known that during acute and chronic inflammation various putative mediators of inflammation are released by the inflamed tissues and by leukocytes. The concentrations of these mediators and leukocytes are indicative of the level or degree of inflammation. Likewise, a reduction in concentration of these mediators and leukocytes is an indication of the effectiveness of a drug in treating inflammation.

Anti-inflammatory steroidal preparations (e.g., corticosteroids) are currently the drug of choice in the treatment of uveitis and other ocular inflammatory conditions. Although there is a wide range of other anti-inflammatory drugs available, only corticosteroids are presently approved for use ill the treatment of ocular inflammation.

The anti-inflammatory action of corticosteroids is thought to be due to interference with arachidonic acid metabolism, i.e., by inhibition of phospholipase $A_2$ which causes the release of arachidonic acid from the tissue phospholipid pool. Although steroids are effective in the treatment of ocular inflammation, their extended use is complicated by severe and numerous side effects. Therefore, it would be highly desirable to develop new nonsteroidal drugs which have a high therapeutic effectiveness but which do not exhibit steroid-like side effects.

It has been previously demonstrated that dexamethasone (a corticosteroid), cyclosporin A (a potent immunosuppressive agent) and rapamycin (an antifungal and immunosuppressive agent) inhibited the corneal graft rejection process in the heterolammelar corneal transplantation model in the rabbit. Current Eye Res., 9:749-757 (1990). In this study, rapamycin was also found to be more potent than cyclosporin A in prolonging the graft survival after cessation of treatment.

Some preliminary clinical studies demonstrated that cyclosporin A may be effective in alleviating inflammatory symptoms in chronic idiopathic uveitis patients, some of whom were resistant to corticosteroid treatment. Am. J. Ophtal., 96:275-282 (1983); Lancet, 2:235-238 (1983). However, numerous cytotoxic side effects are observed with cyclosporin A, most likely due to the large doses of cyclosporin A required to obtain a therapeutic effect.

Accordingly, it is desirable to develop a treatment for ocular inflammation without the deleterious side effects of corticosteroids or cyclosporin A.

Rapamycin, a macrocyclic triene antibiotic produced by *Streptomyces hygroscopicus*, and described in U.S. Pat. No. 3,929,992, incorporated herein by reference, has been shown to prevent the formation of humoral (IgE-like) antibodies in response to an albumin allergic challenge [Martel, R., Can. J. Physiol. Pharm. 55:48 (1977)], inhibit murine T-cell activation [Strauch, M., FASEB 3:3411 (1989)], and prolong survival time of organ grafts in histoincompatable rodents [Morris, R., Med. Sci. Res. 17:877 (1989)].

Figure 1:
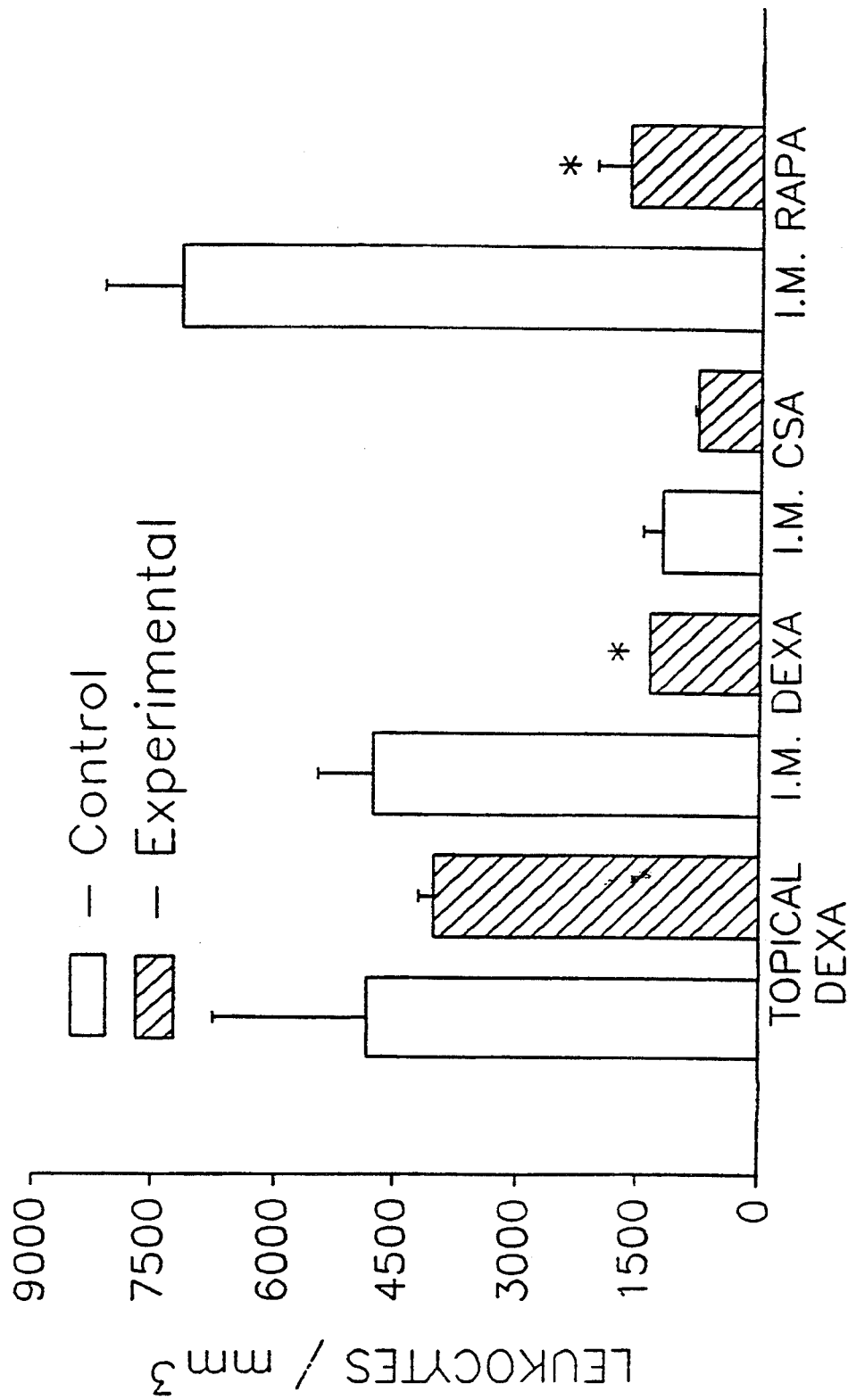
FIG. 1 is a bar graph showing the change in level of leukocytes in aqueous humor after various treatments with dexamethasone, cyclosporin A and rapamycin, compared with controls.

1–5 represent the mean plus SEM (standard error measurement).

SUMMARY OF THE INVENTION

The present invention is directed to a method of treating ocular inflammation in a mammal in need of such treatment, including the administration of an anti-inflammatory amount of rapamycin to the mammal.

DESCRIPTION OF THE INVENTION

The present invention is directed to the treatment of ocular inflammation by the administration of an anti-inflammatory amount of rapamycin. The rapamycin may be administered by any suitable means, including: oral, parenteral, topical, transdermal, rectal, intravenous, intramuscular, intraocular, intravitreal and subcutaneous administration.

In particular, rapamycin is useful in providing symptomatic relief of, preventing the progression of, or eradicating ocular inflammation, associated with, resulting from, or described as, for example, uveitis, conjunctivitis, episcleritis, scleritis, optic neuritis, retrobulbar neuritis, keratitis, blepharitis, and the like; ocular inflammation following ocular surgery; and ocular inflammation resulting from physical eye trauma.

Several standard pharmacological ocular inflammatory models have been used to study anti-inflammatory effects of steroidal and non-steroidal drugs. These include: (1) endotoxin-induced uveitis which is an acute and non-immunogenic model; (2) uveitis induced by bovine serum albumin, which is an immunogenic model; (3) corneal injury model [Kulkarni, P. S., Trends in Pharmacol Sci 8 (10); (1987)]; and (4) corneal heterolamellar transplant model (Guo. A., Curr. Eye Res. 9(8):749 (1990)].

The effect of rapamycin on ocular inflammation was established in an in vivo experiment using the endotoxin-induced uveitis model, which emulates inflammatory eye disorders observed in mammals. The procedure used and results obtained are described below.

EXAMPLE 1

The following experiment demonstrates the effect of dexamethasone, cyclosporin A and rapamycin on endotoxin-induced uveitis in rabbits.

Thirty-two New Zealand male rabbits weighing between 1.5 and 2.0 kg. were used in this study. The rabbits were divided into four groups according to drug treatment. The rabbits were treated according to the guidelines of the use of animal in research by the Association of Research in Vision and Ophthalmology (ARVO) resolution.

Each of the groups was compared to its own vehicle-treated control group, as the grade of uveitis is known to vary from one experiment to another. All rabbits were pre-treated with their respective drugs one hour before intravitreal injection of endotoxin.

*E. coli* endotoxin (LPS) obtained from Sigma Co. (St. Louis, Mo.) was dissolved in sterile physiological saline solution at a concentration of 10 ng./$\mu$l. After cleansing and anesthetizing each eye of the rabbit with topical alcaine (proparacaine HCL) 10 $\mu$l (100 ng) of the LPS was injected intravitreally (using a 30 G needle attached to a Hamilton constant range syringe) into both eyes of each rabbit. All the rabbits were euthanized with an overdose of Pentobarbital Sodium (euthanasia strength) 24 hours after the LPS injection, by which time maximal inflammation has occured. *Trends in Pharmacological Sciences,* 8:375–377 (1987).

Aqueous humor was obtained immediately by paracentesis using a 22 gauge needle containing 50 $\mu$l of heparinized saline. The aqueous humor from both eyes of each rabbit was pooled. The eyes were then enucleated, sectioned around the equator and the iris ciliary body was gently lifted out and divided for radioimmunoassay (RIA) and myeloperoxidase (MPO) assay. The iris ciliary bodies from both eyes of each rabbit were also pooled for the RIA and MPO assays. Cell count, protein determination as well as $PGE_2$ and $LTB_4$ levels were determined from the aqueous humor while $PGE_2$ and $LTB_4$ synthesis and MPO activity were determined from iris ciliary bodies. In each group, the number of samples for each of the assayed mediator as well as for the cell count and protein determination was four.

Drugs and Treatment Regimen

The rabbits were divided into four groups according to drug treatment as follows:

GROUP I:
  Control—Topical 0.9% sterile saline every four hours.
  Experimental—Topical dexamethasone (0.1%) every four hours.

GROUP II:
  Control—intramuscular injection (I.M.) 0.9 % Saline t.i.d.
  Experimental—I.M. dexamethasone (2mg/kg) t.i.d.

GROUP III:
  Control—I.M. Castor Oil b.i.d.
  Experimental—I.M. cyclosporin A (25mg/kg) b.i.d.

GROUP IV:
  Control—I.M. Carboxymethyl Cellulose (CMC)
  Experimental—I.M. rapamycin (10mg/kg. b.i.d.

Absolute values of treatment and control groups were respectively compared using student's unpaired t-test for statistical evaluation.

Dexamethasone was dissolved in sterile physiological saline (0.9%) while cyclosporin A was suspended in castor oil. rapamycin was suspended in carboxymethyl cellulose. All rabbits were given the first dose of their respective drug treatments one hour before intravitreal endotoxin injection and the last dose one hour before euthanasia. The topical dexamethasone group received four additional treatments at four-hour intervals between the first and last treatments. The I.M. dexamethasone group received one more treatment between the first and last while the I.M. cyclosporin A and rapamycin groups received just the first and last treatments only. All I.M. injections were given in the rabbit thigh muscle.

Leukocyte Count

The aqueous humor leukocytes were counted by mixing 5 $\mu$l of the aqueous humor (obtained by a precision microsyringe—Hamilton Co., Reno, Nev.) with 5 $\mu$l of Turk's solution (dilute glacial acetic acid + gentian violet) and placing this mixture on a hemocytometer. The cells were counted using a light microscope.

Protein Determination

The protein concentration of the aqueous humor was measured using 5 $\mu$l of the aqueous humor. BioRad protein assay (BioRad Labs, Richmond, Calif.) was used to determine the protein concentration. BioRad assay is based on the shift of absorbance of Coomassie Brilliant Blue G-250 from 465–595 nm when binding to protein occurs. Absorbance was read using a Beckman DU64 Spectrophotometer.

Measurement of the Release of $PGE_2$ and $LTB_4$ into Aqueous Humor

The concentration of these eicosanoids (biologically active substances derived from arachidonic acid) in the aqueous humor and the incubated iris ciliary body was measured using the respective radioimmunoassay (RIA) Kits (Amersham, Arlington Hts., Ill.). The eicosanoids were extracted from acidified (pH 3) aqueous humor samples in chloroform: Methanol (2:1) mixture. The organic phase was dried under nitrogen ($N_2$) and the samples were reconstituted in the buffer provided in the RIA kits.

Measurement of $PGE_2$ and $LTB_4$ Synthesis in Iris Ciliary Body

The MPO activity in the iris ciliary body was measured according to the method elaborated by Bradley. *J. Invest. Dermatology*, 78:207–209. In this method, the enzyme (MPO) found in the intracellular granules of neutrophils is utilized as a marker for tissue neutrophil content.

Aqueous Humor Leukocyte Content

The effect of the different drug treatments on aqueous humor inflammatory cells in represented in FIG. 1. I.M. dexamethasone produced a highly significant ($P<0.05$) reduction (72%) in the aqueous humor leukocyte as compared with its control group, while topical dexamethasone caused only a 17% decrease in counts. cyclosporin A I.M. reduced the leukocyte counts by 36% while I.M. rapamycin caused a highly significant decrease (77%) in aqueous humor leukocyte.

Aqueous Humor Protein

Figure 2:
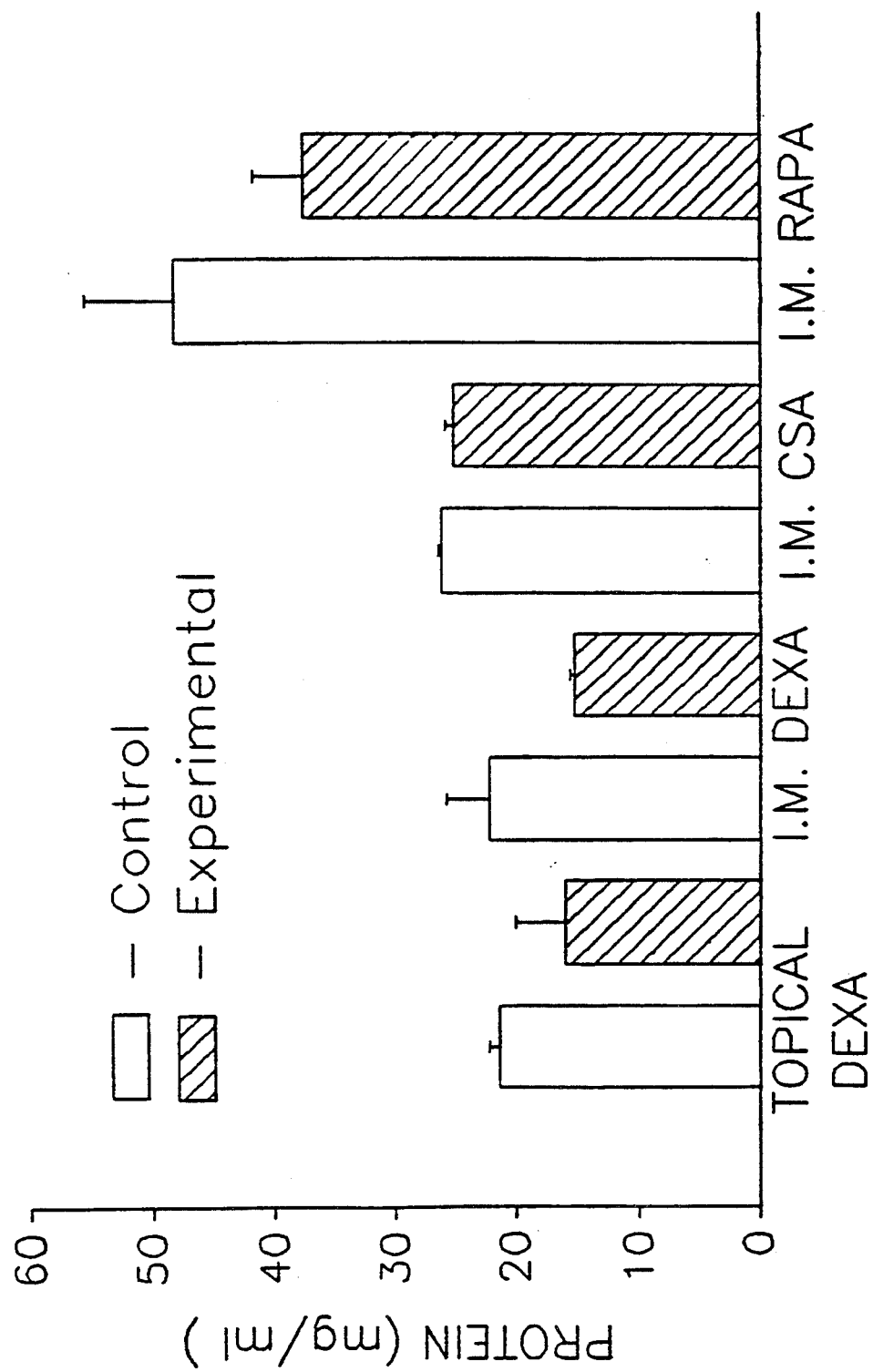
FIG. 2 is a bar graph showing the change in level of protein in aqueous humor after various treatments with dexamethasone, cyclosporin A and rapamycin, compared with controls.

FIG. 2 shows the effect of the drugs on aqueous humor protein concentration. None of the drug treatments significantly reduced the aqueous humor protein concentration ($P>0.05$). I.M. dexamethasone and topical dexamethasone reduced the aqueous humor protein content by 31% and 24%, respectively. I.M. rapamycin decreased the protein level by 22% while I.M. cyclosporin A did not seem to affect the protein level considerably, with only a 4% reduction.

Inflammatory Mediators

Figure 3A:
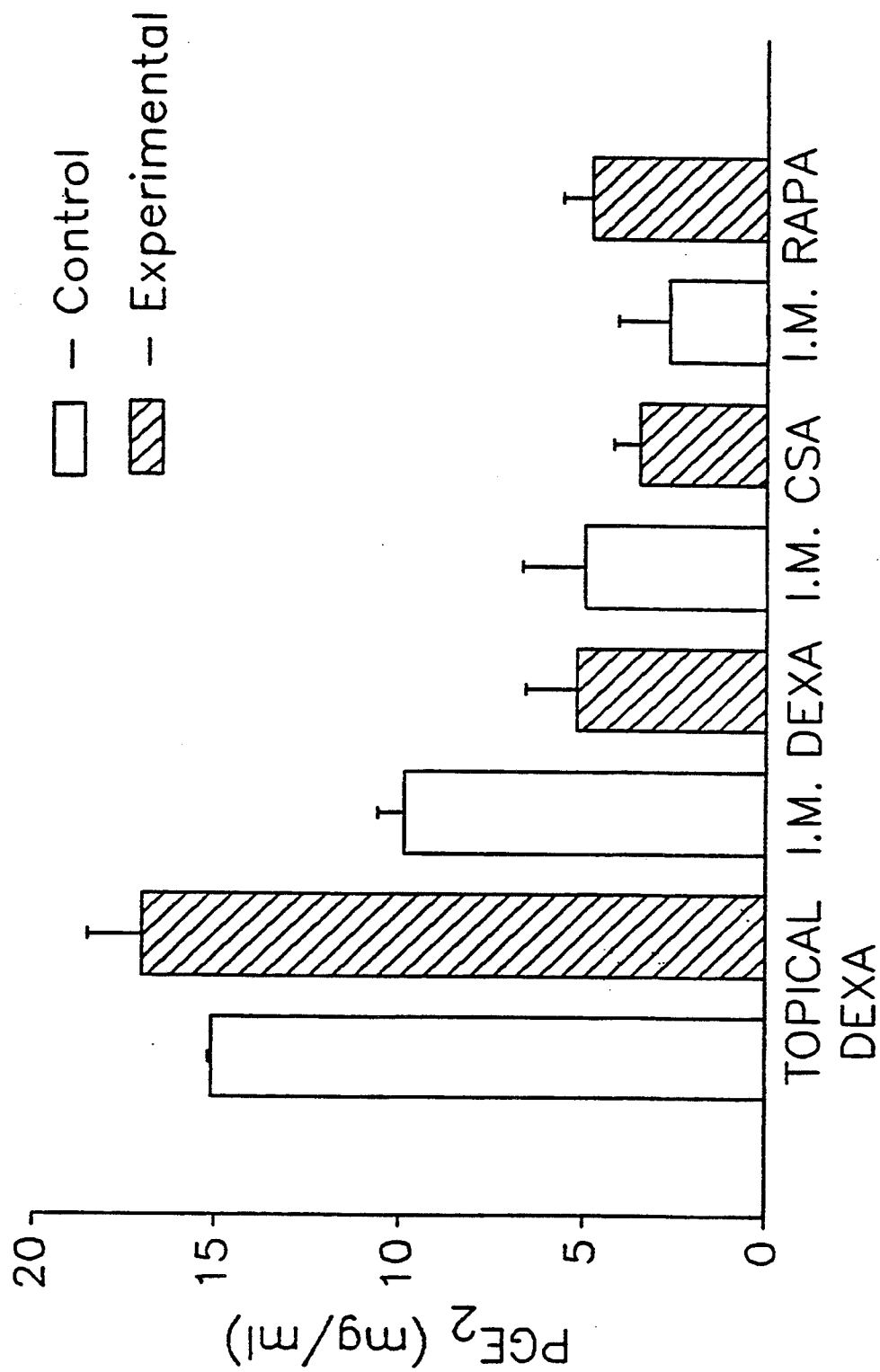
FIGS. 3A and 3B are bar graphs showing the change in levels of $PGE_2$ and $LTB_4$, in aqueous humor, respectively after various treatments with dexamethasone, cyclosporin A and rapamycin, compared with controls.
Figure 3B:
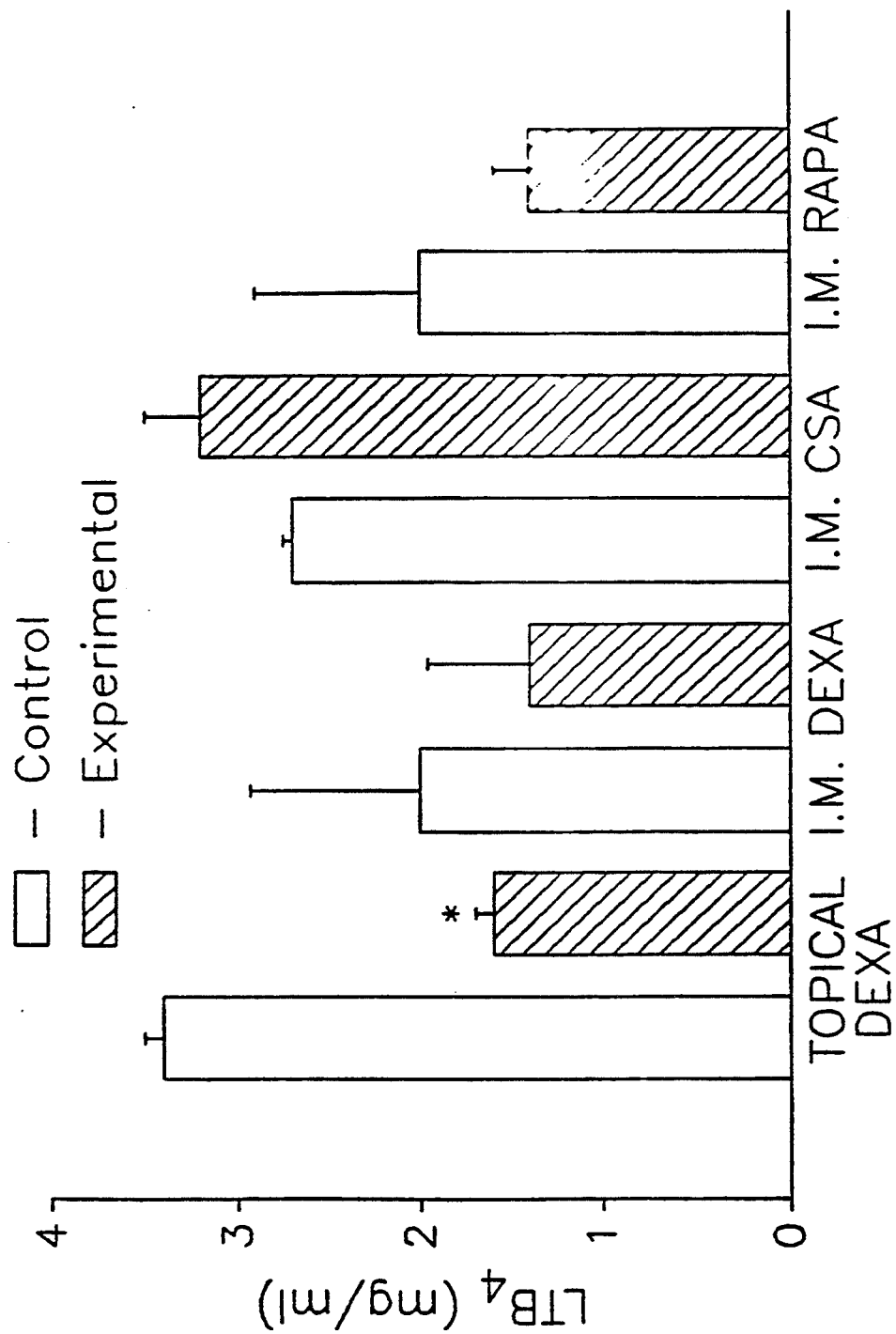
Figure 4A:
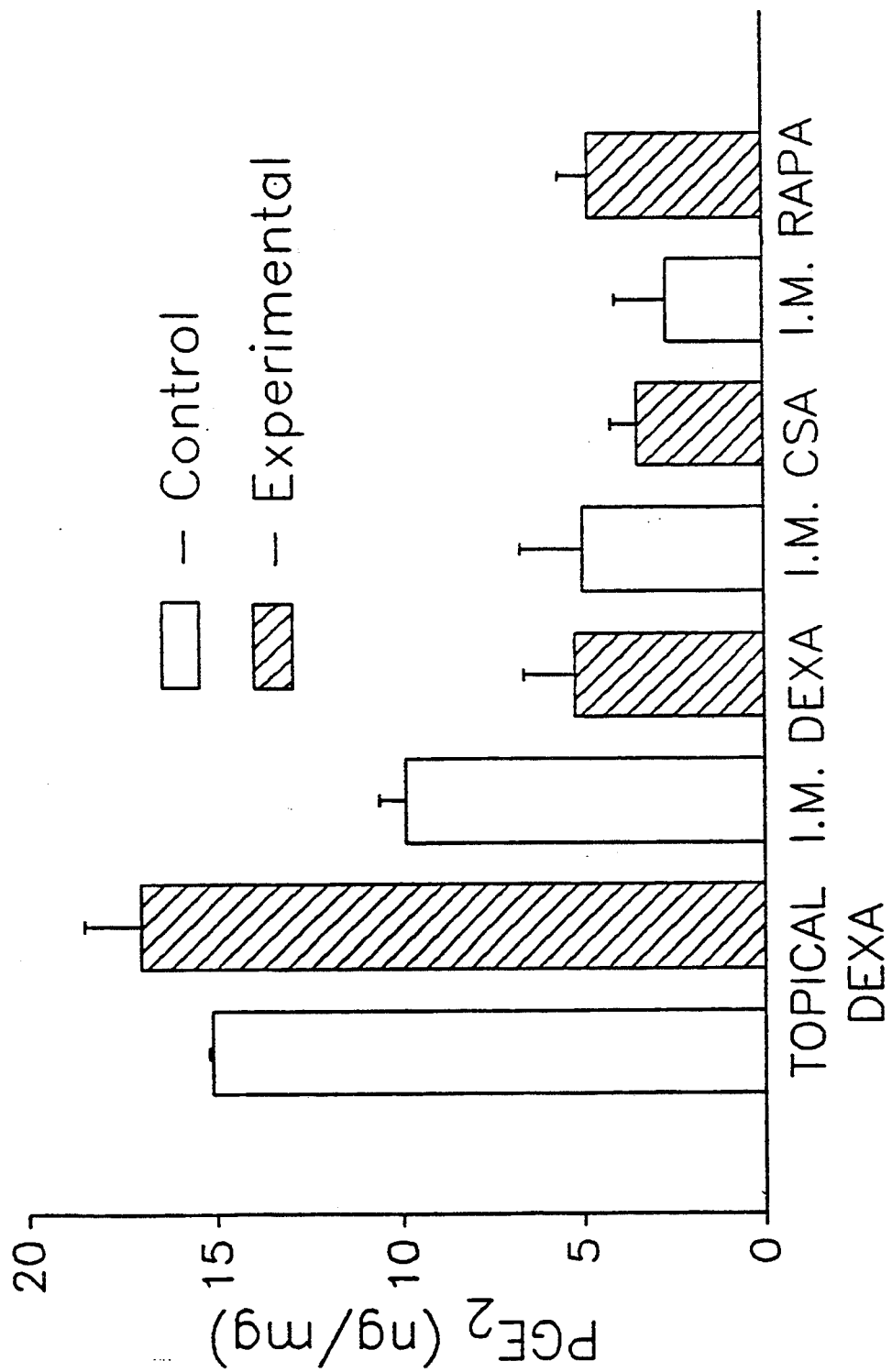
FIGS. 4A and 4B are bar graphs showing the change in levels of iris-ciliary body $PGE_2$ and iris-ciliary body $LTB_4$, respectively after various treatments with dexamethasone, cyclosporin A and rapamycin, compared with controls.
Figure 4B:
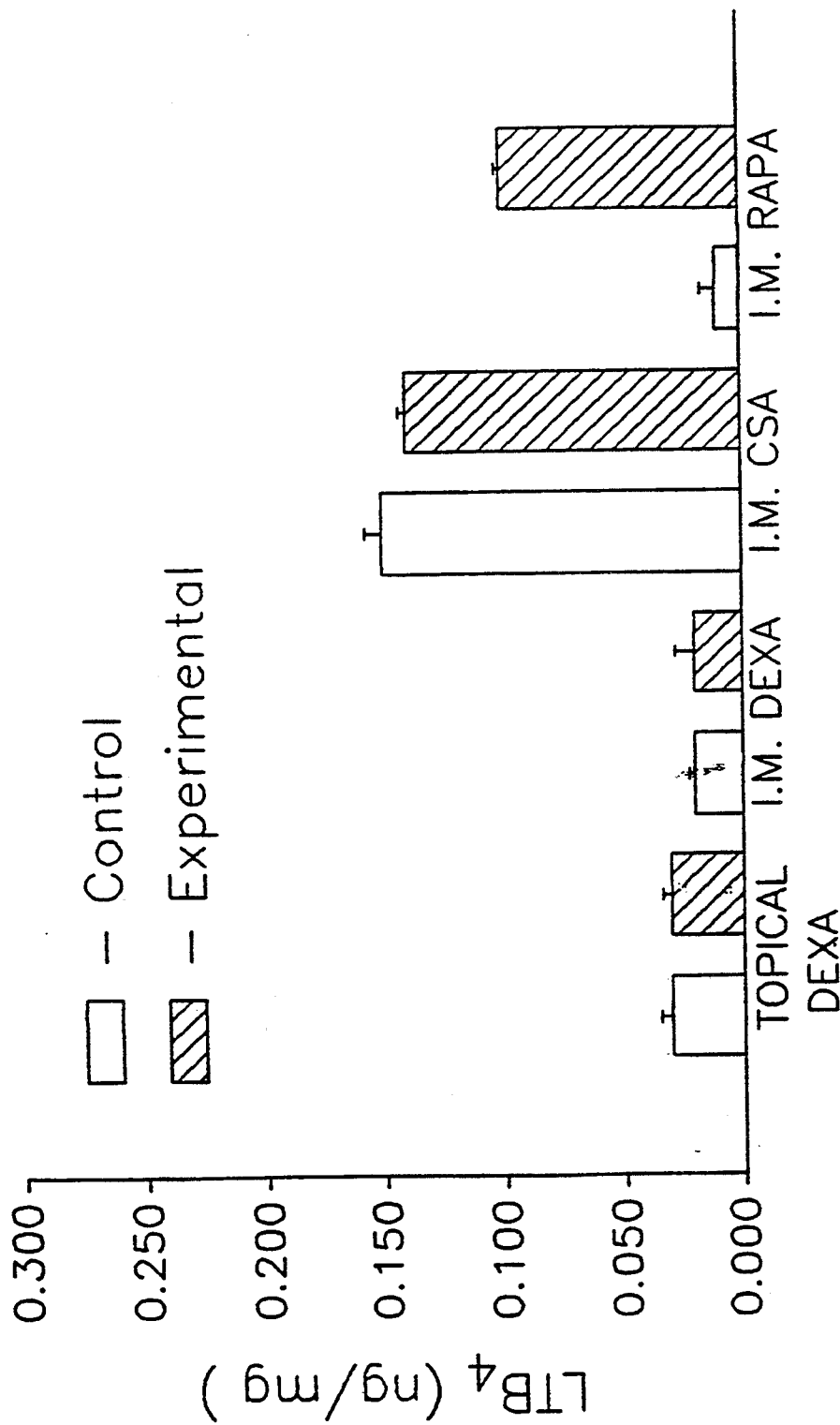

FIGS. 3 and 4 illustrate the effect of drug treatment on the release of $PGE_2$ and $LTB_4$ into aqueous humor and their synthesis in iris ciliary body. I.M. dexamethasone significantly ($P<0.05$) inhibited the $PGE_2$ release into the aqueous humor and iris ciliary body by 54% and 47%, respectively. It did not, however, have a significant effect on the $LTB_4$ levels with an inhibition of only 30% in the aqueous humor. The synthesis of $LTB_4$ in iris ciliary body was not affected by I.M. dexamethasone. Topical dexamethasone had a large effect ($P<0.05$) on the aqueous humor eicosanoid levels. It caused an inhibition of 89% ($PGE_2$) and 67% $LTB_4$ in the aqueous humor. It had no significant effect on the eicosanoid levels in the iris ciliary body. I.M. rapamycin significantly decreased the release of $PGE_2$ into the aqueous humor by 61% while decreasing the aqueous humor $LTB_4$ by 30%. Rapamycin did not affect the eicosanoid levels in the iris ciliary body. Also, I.M. cyclosporin A did not have any significant effect ($P>0.05$) on the aqueous humor eicosanoid levels. In the iris ciliary body, it reduced $PGE_2$ levels by 30% and the $LTB_4$ level by only 7%.

Myeloperoxidase Activity

Figure 5:
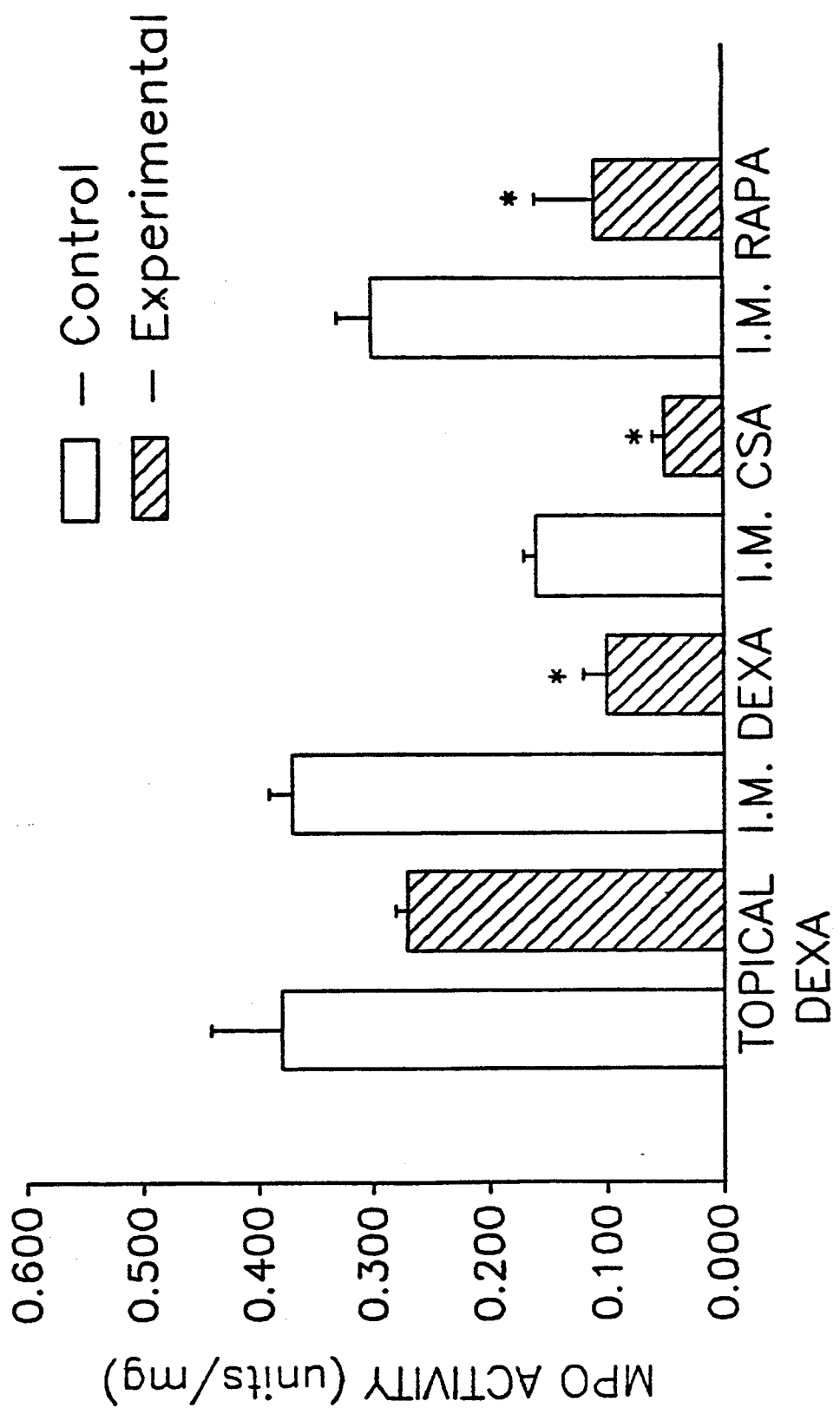
FIG. 5 is a bar graph showing the change in levels of iris-ciliary MPO activity after various treatments with dexamethasone, cyclosporin A and rapamycin, compared with controls. All of the values set forth in FIGS.

FIG. 5 represents the polymorphonuclear neutrophil infiltration into the iris ciliary body as indicated by the myeloperoxidase activity. I.M. dexamethasone, I.M. cyclosporin A and I.M. rapamycin significantly ($P<0.05$) decreased the MPO activity in the iris ciliary body by 73%, 69% and 63%, respectively, while topical dexamethasone reduced the iris ciliary body-MPO activity by only 30%.

In the present study, despite more frequent doses, topical dexamethasone did not significantly affect the leukocyte count in the aqueous humor. However, it significantly inhibited the release of $LTB_4$ into the aqueous humor but not its synthesis in the iris ciliary body (iris ciliary body). The aqueous humor protein as well as myeloperoxidase (MPO) activity in the iris ciliary body were not significantly inhibited by topical dexamethasone. However, I.M. dexamethasone significantly inhibited leukocyte infiltration into the aqueous humor. The aqueous humor protein concentration was lowered, but not significantly. $PGE_2$ release into the aqueous humor and its synthesis by the iris ciliary body were significantly inhibited by I.M. dexamethasone, while the $LTB_4$ levels in both the aqueous humor and iris ciliary body were not affected.

Rapamycin and cyclosporin A were both effective in decreasing the leukocyte response in the aqueous humor. The leukocyte counts in the cyclosporin A group were much lower than those in the other groups. This is probably due to the vehicle (castor oil) that was used. Castor oil is believed to have a mild anti-inflammatory effect in the eyes of animals after removal of a foreign body from the eye. The Merck Index, 8th Edition. Rapamycin and cyclosporin A did not significantly lower the protein content of the aqueous humor nor did they affect the eicosanoid synthesis in the iris ciliary body. The overall anti-inflammatory effect of rapamycin and cyclosporin A was less than that of dexamethasone in this model. However, in this study rapamycin was at least three times more effective than cyclosporin A. Rapamycin has also been found to be three to fifty times more effective than cyclosporin A in inhibiting the graft rejection process in heterotrophic heart, skin and kidney models. *Transplantation and Immunology Letter*, VII:5–7 (1990).

In summary, rapamycin (10 mg/kg bid) given intramuscularly inhibited aqueous humor leukocytes by 67%, $PGE_2$ by 75%, and myeloperoxidase activity in the iris ciliary body by 50%. Cyclosporin A (25 mg/kg bid, intramuscularly) inhibited aqueous humor leukocytes by 36%, iris ciliary body $PGE_2$ by 30%, and myeloperoxidase activity 68%. These results show that rapamycin is useful in preventing or treating inflammatory ocular disorders.

When rapamycin is employed in the treatment of inflammatory ocular disorders, it can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or table-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Rapamycin may be administered rectally in the form of a conventional suppository. Rapamycin may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Rapamycin may be administered topically as a solution, cream, or lotion by formulation with pharmaceutically acceptable vehicles containing 0.1–5 percent, preferably 2%, of active compound.

The dosage requirements vary with the particular compositions employed, the route of administration, the severity of the symptoms presented and the particular subject being treated. Based on the results obtained in the standard pharmaceutical test procedure, projected daily doses of active compound would be about 0.01–50 mg/kg, preferably between about 0.1–35 mg/kg, and more preferably between about 0.3–25 mg/kg. Treatment will generally be initiated with small dosages less than the optimum dose of the compound. Thereafter the dosage is increased until the optimum effect under the circumstances is reached; precise dosages for oral, parenteral, topic, transdermal, or rectal administration will be determined by the administering physician based on experience with the individual subject treated. In general, rapamycin is most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method for treating ocular inflammation in a mammal in need of said treatment, comprising administering to said mammal an effective anti-inflammatory amount of rapamycin.

2. The method according to claim 1 in which said ocular inflammation is selected from the group consisting of uveitis, conjunctivitis, episcleritis, scleritis, optic neuritis, retrobulbar neuritis, ocular inflammation following ocular surgery, and ocular inflammation resulting from physical eye trauma.

3. The method of claim 1, wherein said rapamycin is administered by a route of administration selected from the group consisting of oral, parenteral, topical, transdermal and rectal administration.

4. A method of providing symptomatic relief of, preventing the progression of, or eradicating ocular inflammation in a mammal in need of thereof, comprising administering to said mammal an effective anti-inflammatory amount of rapamycin.

5. A method for treating ocular inflammation in a mammal in need of said treatment, comprising administering to said mammal between about 0.01 and 50 mg/kg/day of rapamycin.

6. The method of claim 5 wherein said rapamycin is administered in an amount of between about 0.1 to 35 mg/kg/day.

7. The method of claim 5 wherein said rapamycin is administered in an amount of between about 0.3 to 25 mg/kg/day.

* * * * *

UNITED STATES PATENT AND TRADEMARK OFFICE
CERTIFICATE OF CORRECTION

PATENT NO. : 5,387,589  
DATED : February 7, 1995  
INVENTOR(S) : Prasad S. Kulkarni Page 1 of 1

It is certified that error appears in the above-identified patent and that said Letters Patent is hereby corrected as shown below:

<u>Column 1,</u>  
Line 7, add:  
-- Research for this invention was made with support from the National Eye Institute of the National Institute of Health Grant Number EY02861. The Government has rights to this invention. --.

Signed and Sealed this

Second Day of May, 2006

JON W. DUDAS  
*Director of the United States Patent and Trademark Office*